US00RE36495E

United States Patent [19]

Blakeley et al.

[11] E Patent Number: Re. 36,495

[45] Reissued Date of Patent: Jan. 11, 2000

[54] RF COIL IDENTIFICATION AND TESTING INTERFACE FOR NMR SYSTEMS

[75] Inventors: Douglas M. Blakeley, Euclid, Ohio; David A. Molyneaux, Gainesville, Fla.

[73] Assignee: Picker International, Inc., Highlands Heights, Ohio

[21] Appl. No.: 09/146,889

[22] Filed: Sep. 2, 1998

Related U.S. Patent Documents

Reissue of:

[64] Patent No.: 5,551,430
Issued: Sep. 3, 1996
Appl. No.: 08/286,780
Filed: Aug. 5, 1994

[51] Int. Cl.[7] ..... A61B 5/055

[52] U.S. Cl. ..... 600/410; 324/318; 324/322

[58] Field of Search ..... 600/410, 421, 600/422; 324/307, 309, 318, 322

[56] References Cited

U.S. PATENT DOCUMENTS 4,972,852 11/1990 Koob et al. ..... 128/653 R
5,065,760 11/1991 Krause et al. ..... 128/653.5
5,144,244 9/1992 Kess ..... 324/322
5,457,387 10/1995 Patrick et al. ..... 324/318
5,461,314 10/1995 Arakawa et al. ..... 324/318

*Primary Examiner*—Brian L. Casler
*Attorney, Agent, or Firm*—Fay, Sharpe, Fagan, Minnich & McKee, LLP

[57] ABSTRACT

A movable patient supporting portion (10) of a patient couch (A) includes a socket (26) for receiving a mating plug (24) on a localized coil (B). The patient couch selectively inserts the localized coil and a supported patient into a bore (14) of a cryogenic magnet system (C). The localized coil includes a resistor (86) whose magnitude identifies the coil. A coil identification interrogator (84) interrogates the coil identification resistor and derives a corresponding binary coil identification. The coil identification addresses a look-up table (90) to retrieve diagnostic test information, an identification of a coil for a human-readable display, and, preferably, an identification of an isocenter of the coil. A diagnostic test unit (92) electrically tests the coil through the plug and socket connection with the diagnostic tests prescribed by the look-up table. A display interface (94) converts error messages from the diagnostic test unit and the coil identification from the look-up table into appropriate format for a display (40). A couch computer (18) controls a motor (20) in accordance with the isocenter of the coil from the look-up table to control positioning of the patient and the localized coil.

30 Claims, 3 Drawing Sheets

RF COIL IDENTIFICATION AND TESTING INTERFACE FOR NMR SYSTEMS

Matter enclosed in heavy brackets [ ] appears in the original patent but forms no part of this reissue specification; matter printed in italics indicates the additions made by reissue.

BACKGROUND OF THE INVENTION

The present invention relates to a radio frequency coil front end interface system for magnetic resonance scanners. The invention finds particular application in conjunction with an intelligent detection and recognition system for identifying and diagnostic testing of a radio frequency coil. The invention also finds application in conjunction with the cable connection system for interconnecting the radio frequency coil and the interface system.

Magnetic resonance imagers commonly include a bore dimensioned to receive a patient to be imaged. The bore is surrounded by a toroidal superconducting magnet for generating a temporally constant magnetic field axially through the bore. Whole body radio frequency and gradient coils typically surround the bore. A patient couch supports and transports the patient into and out of the bore. More specifically, the patient couch is commonly height adjustable. The patient supporting surface is retractable from the bore for positioning the patient thereon and extendible into the bore.

When doing localized scans such as head or heart scans, a localized coil is commonly positioned in the bore with the patient. Cables, typically coaxial cables, are connected between the insertable coil and a radio frequency transmitter and receiver.

U.S. Pat. No. 4,972,852 of Koob discloses a head coil with an 8-pin connector. A selected one or a selected pattern of the pins are connected to ground to provide an 8-binary bit identification of the insertable coil. A digital circuit reads which pins are and arc not shorted to ground as 1's and 0's and uses digital logic gates to indicate to the computer the type of coil installed. One disadvantage of this system is that it is very complex to manage a multiple analog conductor cable because it is large and prone to pick up stray radio frequency signals. Moreover, when one of the wires or contacts fails, an incorrect indication of the nature of the installed coil is provided to the computer. This erroneous indication of the installed coil could cause an imaging sequence to be initiated which could injure the patient or cause damage to the magnetic resonance equipment.

U.S. Pat. No. 5,144,244 of Kess illustrates a decoupling system for radio frequency antennas. A DC current is applied to both the transmit and receive coils which are wired in series such that RF power will only be transmitted into the patient if pin diode couplers in the receive coil arc shorted (when the receive coil is decoupled) or in the normal operating condition. If the receive coil pin diode is open indicating a failure, the transmit coil exhibits a high reflected RF power reflecting RF signal from the transmitter back to the transmitter rather than into the patient. One drawback of this system is that it provides no direct indication of coil failure. The large reflected power may cause the RF amplifier to shut down in one of its fault modes. If the RF transmitter does not shut down, there is no feedback to the remainder of the system that a magnetic resonance imaging sequence is not running normally.

In a Philips T5/S15 magnetic resonance system, a constant voltage source is applied to a pin of a non-RF signal conductor on a surface coil. A set of analog comparators compare this voltage to reference voltages to determine the normal operating mode of the coil, i.e., whether the coil is a receive only coil, a transmit and receive coil, or a multinuclear coil. In response to this comparison, DC signal is applied to the coil to provide appropriate biasing for the identified mode of operation. One drawback to this type of system is that it complicates the connector because extra pins arc needed for identifying the coil type. The system has no check of the level of current in the coil and could indicate an incorrect type of coil. Further, there is no check that the coil is, in fact, functioning in the identified mode.

The present invention contemplates a new and improved front end interface system which overcomes the above-referenced problems and others.

SUMMARY OF THE INVENTION

In accordance with one aspect of the present invention, a magnetic resonance system is provided which has selectively connectable and disconnectable localized coils. Each coil includes an electronic identification element for identifying the type of coil. A front end interface is connected with the coil identifying element.

In accordance with another aspect of the present invention, the front end interface controls a coil diagnostic analysis unit for electronically analyzing the connected coil. The nature of the diagnoses is selected based on the coil identification.

In accordance with another aspect of the present invention, a human-readable display of the type of coil connected is provided for operator verification.

In accordance with another aspect of the present invention, the coil is interconnected with a scan control computer for selecting or limiting scan sequences to appropriate scan sequences for the identified coil type.

In accordance with another aspect of the present invention, the coil identification further provides an indication of the spatial location of the coil isocenter relative to the patient couch and the magnet isocenter. The front end interface is interconnected with an electronic patient couch controls for controlling positioning of the coil assembly within the bore.

In accordance with another aspect of the present invention, a five-pin plug and socket assembly is provided. A five-pin socket assembly is mounted to the patient couch and a plug assembly of up to five pins is connected with the RF coil. One of the pin assemblies is interconnected with the electronic RF coil identification element. The other pin assemblies carry radio frequency signals to or from windings of the insertable coil assembly.

One advantage of the present invention resides in patient safety. Operation of defective coils and operation of coils in an inappropriate mode are prevented.

Another advantage of the present invention is that it simplifies use of the system. Coil identifications and malfunctioning coil warnings are provided to the operator. Remote operator selection of authorized coil modes can be made without moving the patient or entering the scan room.

Another advantage of the present invention is that patients and coils can be positioned automatically without laser alignment and gauging procedures.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
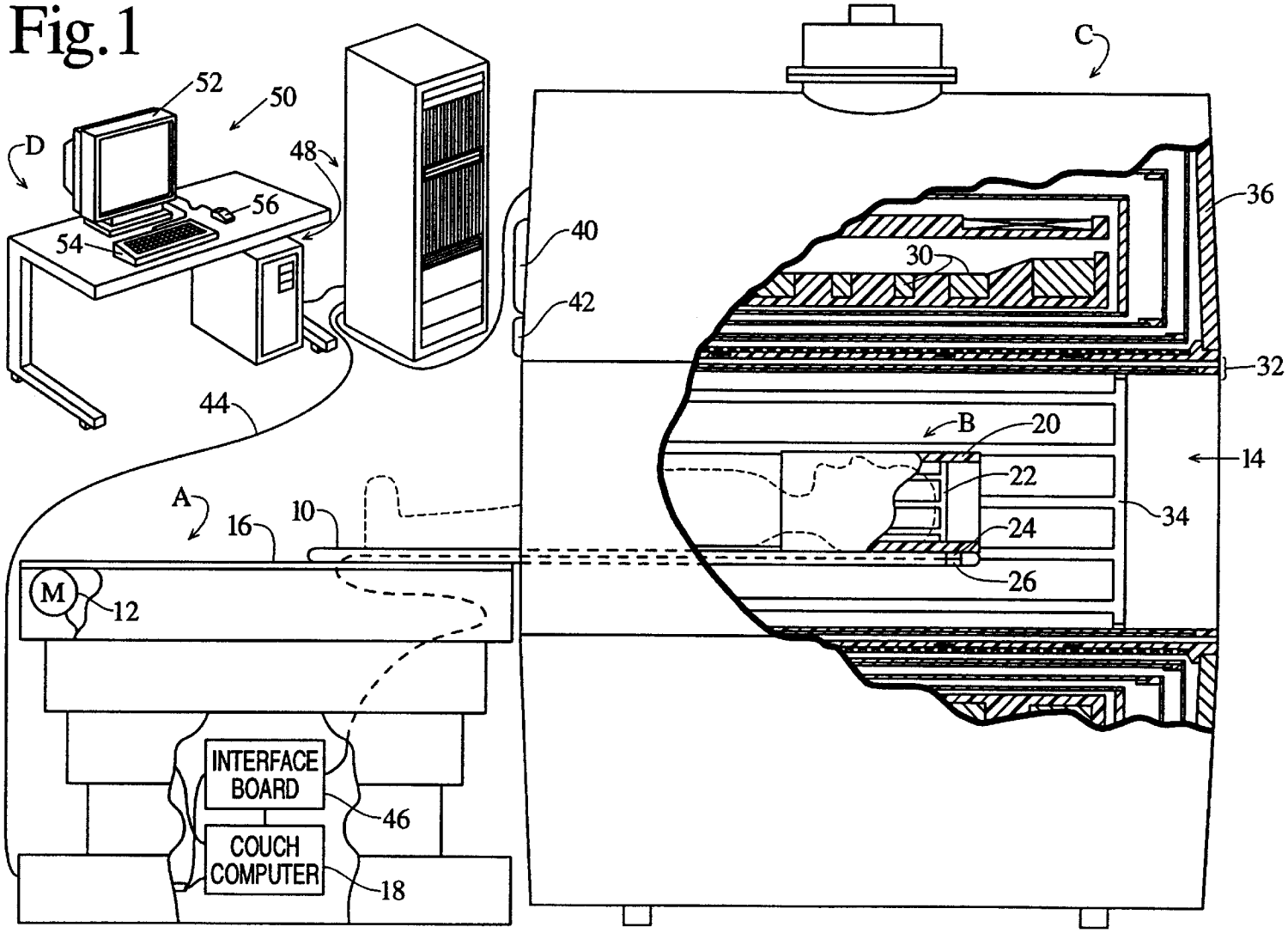
FIG. 1 is a diagrammatic illustration of a magnetic resonance imaging system in accordance with the present invention.

With reference to FIG. 1, a patient couch assembly A selectively inserts and retracts a patient and a localized coil assembly B into and out of an examination region of a cryogenic magnet unit C. The patient couch A includes a patient supporting surface 10 which is drivable by a drive motor 12 or manually movable into and out of a bore 14 of the cryogenic magnet unit. The patient supporting portion 10 is slidably mounted on rails 16 which are connected with a scissor unit or other mechanical system for selectively raising and lowering the patient supporting surface 10. The patient supporting portion 10 is fully withdrawn from the bore to mount a selected one of a plurality of insertable localized coil thereon and position the patient Thereafter, the patient supporting surface is advanced into the bore. Under the control of a couch mounted computer 18, the drive motor 12 selectively advances the patient supporting surface into the bore until an isocenter of the localized coil is at an isocenter of the magnet unit C.

Each localized coil B includes a dielectric former 20 on which a radio frequency coil 22 is supported. A plug 24 is connected with the localized coil for receipt in a socket 26 disposed in the patient supporting surface 10.

The cryogenic magnet unit C includes toroidal magnets 30 for generating a temporally constant magnetic field along a central or z-axis of the bore 12. A whole body gradient coil assembly 32 and a whole body RF coil 34 are mounted around the bore 14. A radio frequency shield separates the whole body gradient and RF coils. Preferably, the magnets 30 are cryogenic magnets which are mounted in a vacuum dewar 36.

An operator display panel 40 is mounted to the vacuum dewar assembly for providing a display to the operator concerning the position of the patient supporting portion 10, the type of RF coil, the location of the RF coil, any errors or defects in the RF coil, and the like. An operator control panel 42 receives operator commands which are communicated to the couch computer 18 for controlling position of the couch top 10, and the like.

A cable 44, preferably a fiber optic cable, provides data communication between the couch computer and a front end interface board 46 disposed within the magnet room and an operator control station D located outside the magnet room in an operator control facility including a front end interface, control and reconstruction computer assembly 48. An operator interface and control station SO includes a human-readable display such as a video monitor S2 and operator input means including a keyboard 54 and a mouse S6.

Figure 2:
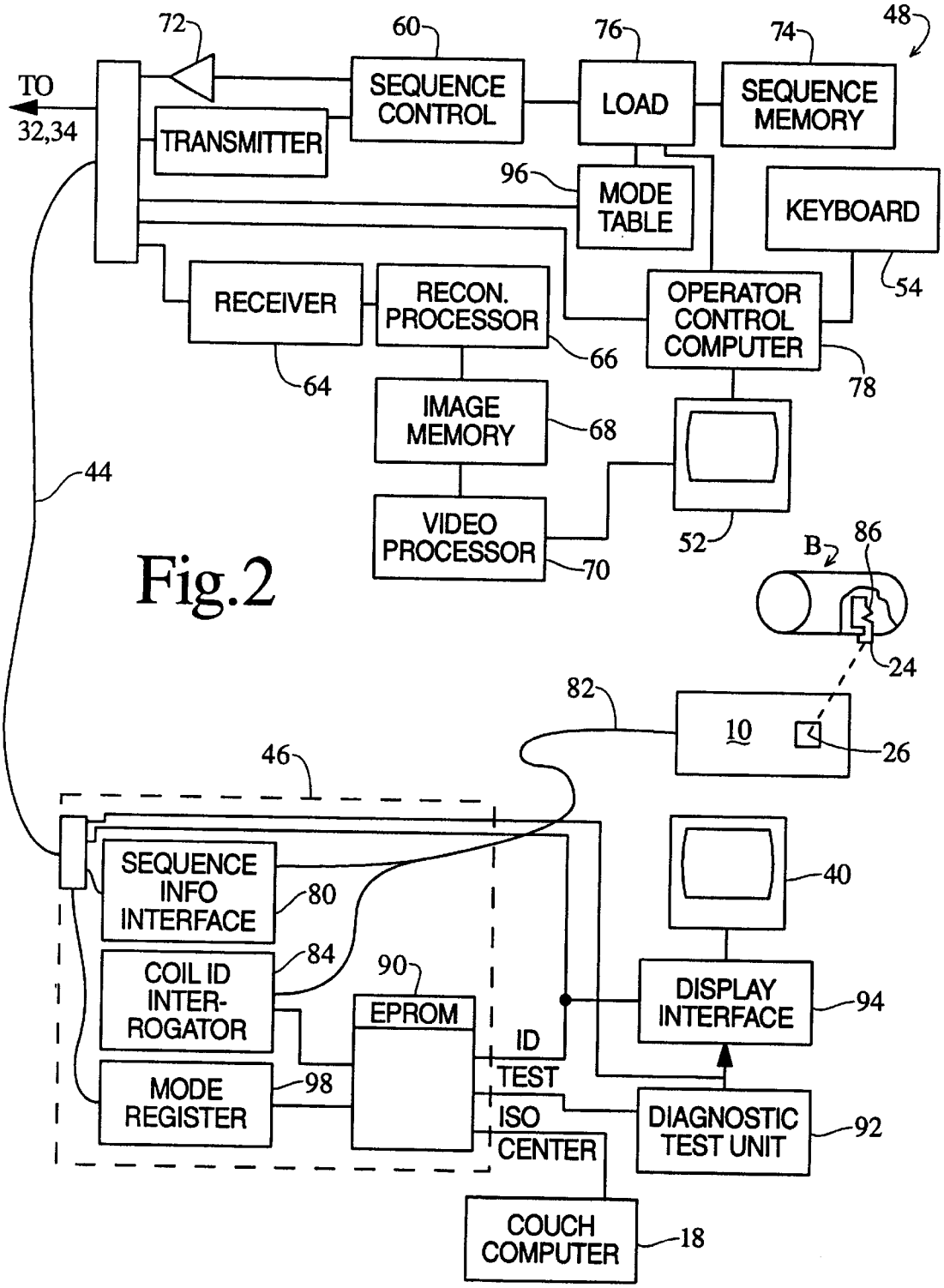
FIG. 2 is a more detailed diagrammatic illustration including details of the front end interface board and related hardware in accordance with the present invention; and, FIGS. 3 and 4 are detailed illustrations of the coil plug and socket assembly.

With particular reference to FIG. 2, the interface, control, and reconstruction computer assembly 48 includes a magnetic resonance sequence controller 60 for controlling magnetic resonance sequences that are applied to the gradient and radio frequency coils. A digital transmitter 62 transmits radio frequency signals under the control of the sequence controller to the radio frequency coils. A digital receiver 64 demodulates the received resonance signals and conveys them to a reconstruction processor 66 which reconstructs the magnetic resonance signals into an image representation which is stored in an image memory 68. A video processor 70 selectively extracts portions of the stored reconstructed image representation and formats the data for display on the video monitor 52. The sequence controller also controls gradient amplifiers 72 which apply current pulses to the gradient coils to create the gradient pulses of the selected magnetic resonance sequence. A sequence memory 74 stores detailed instructions for performing each of the numerous magnetic resonance sequences which the system is programmed to perform. A sequence loading means 76 is controlled by the keyboard or mouse and an operator control computer 78 to load the detailed instructions for a selected sequence into the sequence controller 60 to be performed.

The cable 44 conveys the operator instructions and sequence instructions to the couch computer be and the interface board 46. The interface board 46 includes a sequence information interface 80 which conveys the RF signal switching pulses to a flexible cable 82 which extends through the patient couch assembly to the socket 26. The localized coil B has appropriate internal connections to connect its associated plug with its radio frequency coils. The plug and socket also connect a coil identification interrogation unit 84 with an electronic coil identification component 86, a resistor in the preferred embodiment. Optionally, other encoding components may be provided which provide a digital, frequency, impedance, or other electronically interrogatable identification of the selected coil. The coil identification interrogator 84 converts the coil identification into an appropriate address for a look-up table 90, such as an EPROM.

The coil identification interrogation unit 84 in the preferred embodiment includes a constant current source which applies a constant current across the resistor 86. The constant current is applied when the coil is first connected and periodically to be sure that the coil remains connected. The voltage across the resistor is then compared with a series of preselected voltages. The comparison results are digitized as a binary number which constitutes the ID or address for the look-up table 90. Various other coil identification systems can also be utilized. For example, a constant voltage source could be utilized across the resistor or other impedance. Rather than a characteristic resistance, the coil could use a characteristic inductance or capacitance.

The look-up table 90, when addressed by the coil identification interrogation unit 84, retrieves the corresponding diagnostic testing parameters for the identified coil and loads the retrieved parameters into a diagnostic test unit 92. The diagnostic test unit applies test voltages as prescribed by the diagnostic testing parameters to the localized coil B via cable 82. The diagnostic testing is performed before scanning begins and between magnetic resonance scans. Moreover, the coil is monitored during the scans to assure that the coil continues to function properly. In response to the diagnostic testing determining that there is an error, a corresponding error signal is generated. A display interface 94 receives the error signal and generates a corresponding human-readable display on the monitor 40. The error signal is also fed back to cable 44 to generate a corresponding display on the video monitor S2 and, where appropriate, causes the control computer 78 to stop the scan. The diagnostic test unit 92 is preferably also interconnected with the whole body RF coils to monitor their operation. The display interface 94 is further connected with the look-up table 90. In response to the binary coil identification from the coil interrogator, the look-up table further retrieves instructions for a preselected text description of the coil which is conveyed to the display interface to generate a human-readable identification of the coil.

The coil identification interrogator also conveys the coil identification on the cable 44 to an acceptable mode look-up to table 96. Optionally, the acceptable mode look-up table 96 can be incorporated into the look-up table 90. The acceptable mode look-up table 96 interacts with the sequence loading means 76 such that only sequences which are permitted for the identified coil arc loaded into the sequence controller 60. The acceptable mode table 96 acts as an interlock to lock out all but a selected list of modes, may be interrogated by the loading means 76 to determine which sequences are acceptable to be loaded, or the like.

The localized radio frequency coil B may be any type of receive, transmit, or transmit and receive coil of any geometry or configuration. It may contain multiple RF coils which operate in a simultaneously or switched array topology. The RF cable 82 may be a single coaxial cable of any diameter or multiple cables as may be appropriate to the insertable coil.

Some of the localized coils are connected to the patient support surface by flexible cables, making their position indefinite. However, others are attached to the patient support surface in a fixed position. For those localized coils that have a fixed position on the support surface 10, the EPROM 90 further retrieves an identification of the isocenter of the localized coil. The EPROM 90 is connected with the couch computer 18 to convey the isocenter information thereto for automatic positioning and reference.

For coils which have more than one mode of operation, the selected mode information is conveyed by cable 44 to a mode register or memory 98. The selected mode of operation is conveyed from the EPROM 90 to select the appropriate test instructions for the diagnostic testing unit 92. The operating modes can be set either by the couch computer 16 or the system computer 78 via the bus 44. The bus is preferably a serial data and clock bus which daisy chains through several parts of the MR system. Preferably the bus is a multi-master bus with a defined protocol to permit different masters to have control of the bus. The couch and system computers can each act as masters and all of the devices act as slaves to the bus.

After a valid coil is detected and identified, the interface operating mode is selected by writing the selected mode into the mode register 98 on the interface 46. The mode is read back from the register 98 to the system computer 78 to verify that the proper test procedures have been selected. The coil is tested by turning the test bit on and off in the register. The test mode validates the channels of the coil which are plugged into the couch as well as the whole body coil and the radio frequency signal transmit/receive switch in the sequence information interface 80. The results of the coil test are also stored in the mode register 98 to be read by the system computer. If an invalid status or error is determined by the test unit, the display interface 94 displays the appropriate error message on the couch display 40.

The front end interface 48 provides the primary link to the bus 44. The front end interface provides communication to the couch computer to turn it off during a scan, to command horizontal and vertical motion of the couch, and to determine the current position of the couch. The couch position is used lo set up array coils, and the like. Communication with the couch mounted interface 46 determines which coil is installed on the couch and causes the testing to be performed on the coil.

Some functions are preferably duplicated between the couch computer 18 and the front end interface 48, for example, detection of the coil identification resistor and subsequent testing of the coil. The main system computer initiates several tasks through the front end interface prior to initiation of a scan. For example, the scan computer measures the identification resistor directly over the bus 44 and notifies the operator of the coil or lack thereof. After a valid coil is detected, the primary system computer selects and tests the interface operating mode by writing the mode associated with that coil into the mode register 98. The mode is read back from the mode register to verify that the test mode has been properly set. The coil is tested as before by turning the test bit on and off in the register 98. The test mode validates all channels of the coil which are plugged into the couch, as well as the body coil and the power transmit/receive switch in the sequence information interface 80. The results of the coil test arc read into the system computer. If there is an error or invalid coil status, the appropriate error message is displayed. The default operating mode is selected by writing the mode associated with the coil into the mode register 98 and reading back the mode from register 98 lo verify that the operating mode has been properly selected.

The interface board 46 is interlocked with an RF enable signal to a power signal in the sequence interface 80. During the transmit period, the interface board 46 checks to make sure that the bias current is flowing at the correct levels in the body coil, the high power radio frequency transmit/receive switch, and any coils plugged into the couch connector 26. During the receive enable period, the body coil and the high power transmit/receive switch are checked in a similar manner. The diagnostic interface provides the primary link to the bus 44 during system power-up/down sequences and during the system diagnostics. The diagnostic interface further provides communication to the couch computer 18 to initiate diagnostic functions. Communication with the interface 46 determines which coil is installed on the couch and performs tests of the coil during diagnostic functions. Communication of the radio frequency amplifier determines whether it is operating properly and performs any functional diagnostic tests of its internal sub-systems. Communications to the system computer initiate diagnostic functions. Communications to the gradient amplifier also initiate diagnostic functions.

Figures 3, 4:
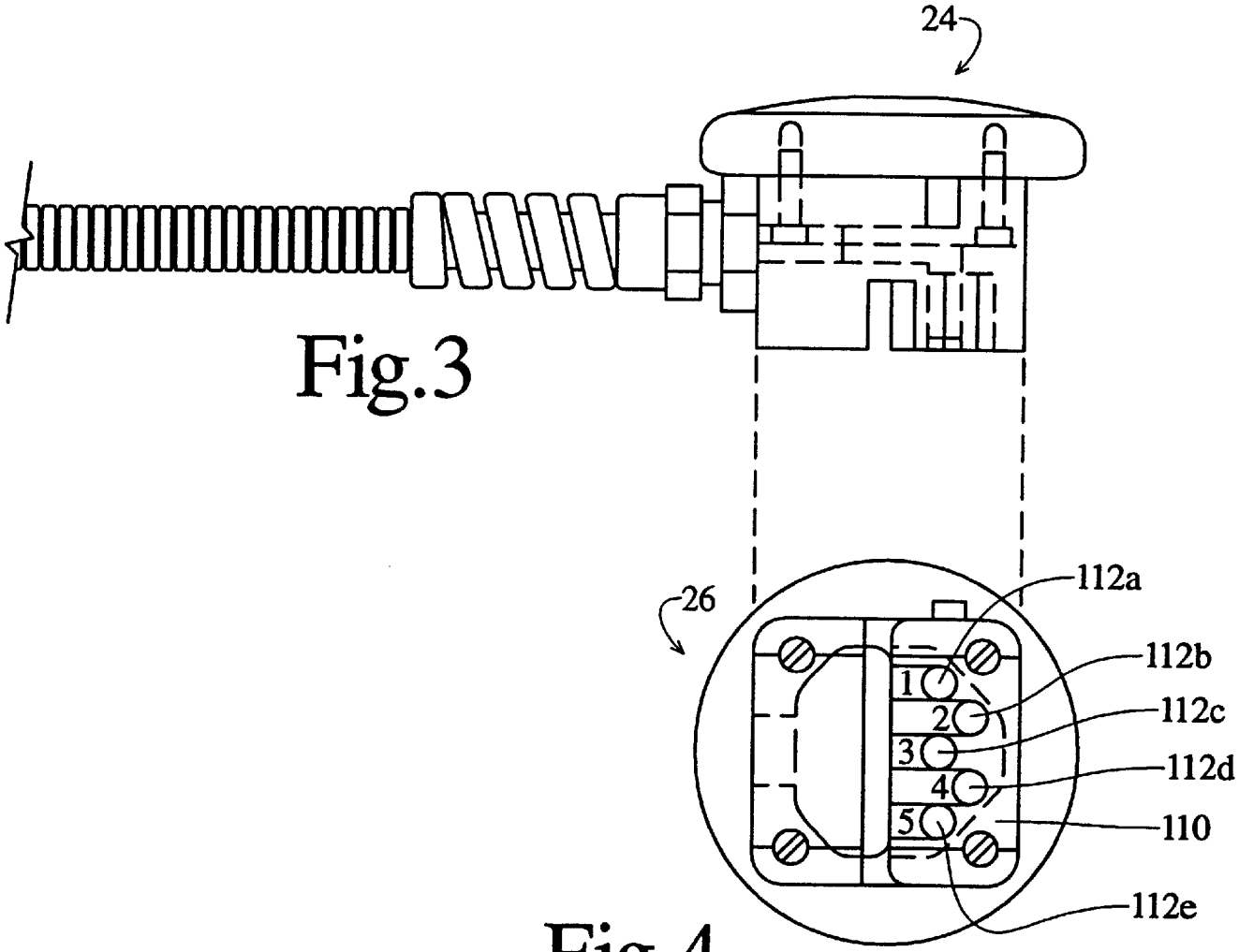

With reference to FIGS. 3 and 4, the socket 26 preferably includes a Delrin housing block 110 which has five bores 112a, 112b, 112c, 112d, and 112e. The bores hold a plurality of RF coaxial contacts which slide on a mating set of RF coaxial contacts. These contacts consist of small non-magnetic coaxial connectors designed to solder or crimp to standard cables. The connectors are held in place using the Delrin connector block. The coil plug 24 also has a Delrin connector block but need not have five mating coaxial connectors. Rather, only the number of coaxial connectors necessary to identify and operate the coil are commonly provided.

An array of five contacts equally spaced in a zigzag configuration are utilized. Positive engagement is assured by the friction between the plug and socket. Four of the contacts carry RF and DC signals and the fifth contact is interconnected with the coil identification component.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A magnetic resonance system comprising:

a primary magnet system for generating a temporally constant magnetic field through an examination region;

a patient couch including a patient supporting portion for selectively positioning a patient and an insertable coil within the examination region;

a plug and socket assembly connected to the patient supporting portion and the insertable coil, respectively, such that the insertable coil is plugged into the patient supporting portion with electrical cabling for the insertable coil extending down the patient supporting portion;

a coil identification component mounted in the insertable coil in electrical connection with the plug and socket assembly; and, a coil identification component interrogator in electrical connection with the plug and socket assembly for interrogating the coil identification component for determining an identification of the inserted coil.

2. The magnetic resonance system as set forth in claim 1, further comprising:

a display interface for generating a human-readable display identifying the insertable coil in accordance with the coil identification determined by the coil identification component interrogator.

3. The magnetic resonance system as set forth in claim 1, further comprising:

a diagnostic testing unit electrically connected to the plug and socket assembly for electrically testing the insertable coil, the diagnostic testing unit being controlled in accordance with the coil identification determined by the coil identification component interrogator to perform tests appropriate to the insertable coil whose identification was determined by the coil identification component interrogator.

4. The magnetic resonance system as set forth in claim 3, further comprising:

a display interface connected to the diagnostic testing unit for converting test failure signals therefrom into an so error message for display to the operator.

5. The magnetic resonance system as set forth in claim 3, further comprising:

a look-up table which is addressed by the coil identification interrogator to retrieve diagnostic test descriptions for the diagnostic testing unit.

6. In a magnetic resonance system which includes a primary magnet system for generating a temporally constant magnetic field through an examination region, a patient supporting portion for selectively positioning a patient and a localized coil within the examination region, the improvement comprising:

a plug and socket assembly connected to the patient supporting portion and the localized coil such that the localized coil is plugged into the patient supporting portion with electrical cabling for the localized coil extending along the patient supporting portion, the plug and socket assembly including a socket with five coaxial interconnections disposed in a zigzag pattern and a plug with up to five coaxial interconnections matingly disposed in the zigzag pattern.

7. A magnetic resonance imaging system comprising:

a magnet assembly for generating a temporally constant magnetic field through an examination region;

a patient couch including a patient supporting portion which is selectively insertable into and removable from the patient examination region;

a localized coil which is selectively disposed on the movable patient supporting surface, the localized coil including an electronically interrogatable coil identification component;

an interface board interconnected with a cable and the localized coil, the interface board including a coil identification interrogator which is electrically connected to the coil identification component for determining an identification of the localized coil, the interface board further communicating radio frequency signals between the localized coil and the cable.

8. The magnetic resonance system as set forth in claim 7 further including:

a receiver connected to the cable for demodulating the radio frequency signals from the localized coil;

a reconstruction processor for reconstructing the demodulated radio frequency signals into an image representation, and a monitor for converting the image representation into a human-readable display.

9. The magnetic resonance system as set forth in claim 7 further including:

a look-up table connected to the coil identification interrogator, the look-up table being controlled by the coil identification interrogator for retrieving preselected information concerning the localized coil.

10. The magnetic resonance system as set forth in claim 9 wherein the look-up table retrieves diagnostic test information for testing the localized coil and further including:

a diagnostic test unit electrically connected to the localized coil for performing electronic diagnostic tests thereon in accordance with the diagnostic test information retrieved from the look-up table.

11. The magnetic resonance system as set forth in claim 10 wherein the localized coil has a plurality of selectable modes, the look-up table further being addressed by a selected one of the plurality of modes such that the diagnostic test information conveyed to the diagnostic test unit is specific to the identified localized coil and the selected mode.

12. The magnetic resonance system as set forth in claim 9 wherein the look-up table retrieves coil information concerning the identified localized coil and further including:

a display controller for converting the retrieved coil information into a human-readable display.

13. The magnetic resonance system as set forth in claim 10 wherein the localized coil is fixedly attached to the patient supporting portion and the look-up table retrieves an identification of an isocenter of the localized coil and the system further including:

a motor for selectively moving the patient supporting portion into and out of the examination region; and, a couch computer which controls the motor, the couch computer being preprogrammed with an isocenter of the magnet assembly which creates the temporally constant magnetic field and being connected to the look-up table to receive the localized coil isocenter therefrom, the couch computer controlling the motor to position the localized coil isocenter at an isocenter of the magnet assembly.

14. A magnetic resonance imaging system as set forth in claim 9 further including a socket physically mounted in the patient supporting surface and a plug connected to the localized coil, the plug and socket frictionally interconnecting to provide an electrical interconnection between the localized coil and the interface board.

15. The magnetic resonance system as set forth in claim 14 wherein the socket includes five electrical connectors arranged in a zigzag pattern, each interconnected with the interface board and the plug includes at least two electrical connectors for frictional and electrical interconnection with the socket electrical connectors.

16. A magnetic resonance method comprising:

positioning an insertable radio frequency coil on a movable patient supporting surface of a patient couch, the radio frequency coil including a coil identification electrical component which identifies the radio frequency coil;

electrically connecting the radio frequency coil with an interface board;

interrogating the coil identification electrical component with circuitry disposed at the interface board to identify the radio frequency coil;

positioning the radio frequency coil in a temporally constant magnetic field in an examination region; and conducting a magnetic resonance examination of a portion of a patient disposed in the examination region using the radio frequency coil.

17. The method as set forth in claim 16 further including:

retrieving diagnostic test parameters based on the coil identification;

testing the radio frequency coil in accordance with the retrieved test parameters.

18. The method as set forth in claim 16 further including deriving and displaying a human-readable identification of the radio frequency coil in accordance with the interrogating step.

19. The method as set forth in claim 16 wherein the electrical connecting step includes inserting a plug which is connected to the radio frequency coil into a socket that is mounted to the patient supporting surface.

20. The method as set forth in claim 16 further including:

rigidly attaching the radio frequency coil to the patient support portion; and, using the coil identification to retrieve an indication of the isocenter of the radio frequency coil within a coordinate system of the patient couch.

21. An insertable coil assembly for interconnection with a magnetic resonance system which includes a primary magnet system for generating a temporally constant magnetic field through an examination region, a patient supporting portion for selectively positioning a patient and the insertable coil assembly within the examination region, a control and reconstruction computer assembly, and a socket with five coaxial interconnections disposed in a zigzag pattern, the socket being mounted to the patient supporting portion and connected by electrical cabling that extends along the patient supporting portion to the control and reconstruction computer assembly, the insertable coil assembly comprising:

a localized coil; and a plug with up to five coaxial interconnections disposed in a zigzag pattern that matingly matches the zigzag pattern of the socket, the plug being connected to the localized coil.

*22. The insertable coil assembly as set forth in claim 21 further including:*

*a coil identification component connected with one of the five coaxial interconnections of the plug.*

*23. The insertable coil assembly as set forth in claim 22 wherein the coil identification component includes a resistor having a preselected resistance value to identify the localized coil.*

*24. An insertable coil assembly for interconnection with a magnetic resonance imaging system which includes a primary magnet system for generating a temporally constant magnetic field through an examination region, a patient supporting portion for selectively positioning a patient, and the insertable coil assembly within the examination region, a control and reconstruction computer assembly, and a socket having a plurality of coaxial interconnections, the coaxial interconnections being interconnected with the control and reconstruction computer assembly, the insertable coil assembly comprising:*

*a plug having a plurality of coaxial interconnections disposed in a pattern that matingly engages the coaxial interconnections of the socket;*

*a coil identification component in electrically connected with one of the coaxial interconnections of the plug; and,*

*a localized coil electrically connected with other of the coaxial interconnections of the plug.*

*25. An insertable coil assembly for interconnection with a magnetic resonance imaging system which includes a primary magnet system for generating a temporally constant magnetic field through an examination region, a patient supporting portion for selectively positioning a patient, and the insertable coil assembly within the examination region, a control and reconstruction computer assembly, and a magnetic resonance imaging system electrical interconnection assembly for conveying electrical signals to and from the control and reconstruction computer assembly, the insertable coil assembly comprising:*

*RF coil windings;*

*a coil identification component; and,*

*an insertable coil electrical interconnection assembly connected with the RF coil windings and a coil identification component, the insertable coil electrical interconnection assembly being detachably connectable with the magnetic resonance system electrical interconnection assembly.*

*26. The insertable coil assembly as set forth in claim 24 wherein the magnetic resonance system and insertable coil electrical interconnection assemblies include a plug and a socket.*

*27. The insertable coil assembly as set forth in claim 24 wherein the coil identification component is an electrical impedance whose resistance identifies the insertable coil.*

*28. A localized RF coil for selective interconnection with an interface board in a magnetic resonance scanner and having a common socket configured for receiving a plug having a plurality of RF signal pins in a preselected configuration including at least one coil identification pin, the localized coil comprising:*

*a plug having a plurality of pins in a preselected configuration for selective receipt in a common plug;*

*at least one RF winding connected with preselected pins of the plug; and,*

*an identification component having characteristic impedance which identifies the localized coil, the identification component being connected with at least one preselected pin of the plug.*

*30. The localized coil, as set forth in claim 29, wherein the identification component further includes:*

*an interrogatable digital data component which responds to interrogation to identify the localized coil.*

*29. A localized RF coil for selective interconnection with an interface board having a common socket configured for receiving a plug of any of a plurality of interchangeable different localized RF coils in a magnetic resonance scanner, the localized RF coil including:*

*an identification component for identifying the localized RF coil;*

*RF windings for at least receiving RF signals; and,*

*a plug interconnected with the RF windings and the identification component, the plug having a pin configuration for matingly engaging the common socket in the magnetic resonance scanner.*

*30. The localized coil, as set forth in claim 29, wherein the identification component further includes:*

*an interrogatable digital data component which responds to interrogation to identify the localized coil.*

* * * * *